(12) United States Patent
Ketterle et al.

(10) Patent No.: US 6,966,978 B2
(45) Date of Patent: Nov. 22, 2005

(54) SENSOR ELEMENT OF A GAS SENSOR

(75) Inventors: Karl-Michael Ketterle, Ludwigsburg (DE); Bernd Schumann, Rutesheim (DE)

(73) Assignee: Robert Bosch GmbH, Stuttgart (DE)

(*) Notice: Subject to any disclaimer, the term of this patent is extended or adjusted under 35 U.S.C. 154(b) by 0 days.

(21) Appl. No.: 10/267,541

(22) Filed: Oct. 9, 2002

(65) Prior Publication Data

US 2003/0075441 A1 Apr. 24, 2003

(30) Foreign Application Priority Data

Oct. 9, 2001 (DE) ................ 101 49 739

(51) Int. Cl.[7] .......................... G01N 27/407
(52) U.S. Cl. .............. 204/427; 204/425; 204/426
(58) Field of Search ................ 204/421–429

(56) References Cited

U.S. PATENT DOCUMENTS

| | | | | |
|---|---|---|---|---|
| 4,902,400 A | | 2/1990 | Usami et al. | |
| 5,314,604 A | * | 5/1994 | Friese et al. | 204/410 |
| 5,474,665 A | * | 12/1995 | Friese et al. | |
| 5,672,811 A | * | 9/1997 | Kato et al. | |
| 5,902,470 A | * | 5/1999 | Schneider et al. | |
| 6,010,615 A | * | 1/2000 | Kato et al. | 205/784.5 |
| 6,036,841 A | * | 3/2000 | Kato et al. | |
| 6,303,011 B1 | * | 10/2001 | Gao et al. | 204/425 |
| 6,332,965 B1 | * | 12/2001 | Sugiyama et al. | 204/425 |

* cited by examiner

Primary Examiner—Kaj K. Olsen
(74) Attorney, Agent, or Firm—Kenyon & Kenyon

(57) ABSTRACT

A solid electrolyte-based sensor element of a gas sensor for determining a gas component in a gas mixture is described, in particular for determining the concentration of oxygen and/or nitrogen oxides in exhaust gases of internal combustion engines. The sensor element has an electrochemical cell that includes a first and a second electrode, both electrodes being located in internal gas spaces of the sensor element. The internal gas space in which the first electrode is located is largely in the same layer plane of the sensor element as at least one other internal gas space of the sensor element in which the second electrode or a reference electrode are located.

15 Claims, 3 Drawing Sheets

SENSOR ELEMENT OF A GAS SENSOR

FIELD OF THE INVENTION

The present invention concerns a sensor element of a gas sensor for determining the concentration of a gas component in a gas mixture.

BACKGROUND INFORMATION

Solid electrolyte-based gas sensors, by which the concentration of individual gas components can be determined electrochemically, have been used for some time in the analysis of exhaust gases of internal combustion engines. The mode of operation of some of these gas sensors is based on the fact that the oxygen concentration within one sensor element integrated into the gas sensor is set at a constantly low value. This is accomplished by an electrochemical pumping process in which oxygen transfer takes place between the electrodes of an electrochemical pumping cell. One of the electrodes of the pumping cell is located on the sensor element's outer surface that is exposed to the exhaust gas. Although this outer pumping electrode is frequently provided with a porous protective coating, it is nonetheless exposed to the corrosive effects of the hot combustion exhaust gases.

U.S. Pat. No. 4,902,400 describes a sensor element in which the oxygen concentration within the sensor element is set at a constant value, without the sensor element having an outer pumping electrode attached to the outside of the sensor element. Instead, the sensor element includes two additional solid electrolyte layers and an additional reference gas duct that is in contact with the ambient atmosphere through an opening and in which the outer pumping electrode is located. This sensor element design is complex, however, and therefore cost-intensive.

The object of the present invention is to provide a sensor element whose outer pumping electrode is not directly exposed to the gas mixture under analysis and which at the same time has as simple a design as possible.

SUMMARY OF THE INVENTION

The sensor element according to the present invention is distinguished by its comparatively simple design and by the fact that all pumping electrodes are located in the internal gas spaces of the sensor element. This permits low-cost manufacture of the sensor element and, at the same time, a long service life for the pumping electrodes that are used. The simple design is achieved by locating the outer pumping electrode in a separate internal gas space of the sensor element, the gas space being integrated into a layer plane of the sensor element in which another internal gas space of the sensor element or a reference gas duct is already located.

Advantageous refinements of and improvements on the sensor element are possible. For example, the internal gas space in which the outer pumping electrode is located may be in contact with a reference gas atmosphere and thus all contact with the corrosive gas mixture atmosphere may be prevented. In another especially advantageous embodiment, the internal gas space in which the outer pumping electrode is located is in contact with the ambient air via a porous electrode lead. This permits a favorable geometry of the internal gas space in which the outer pumping electrode is located and, simultaneously, adequate ventilation of the internal gas space.

DETAILED DESCRIPTION

Figure 1:
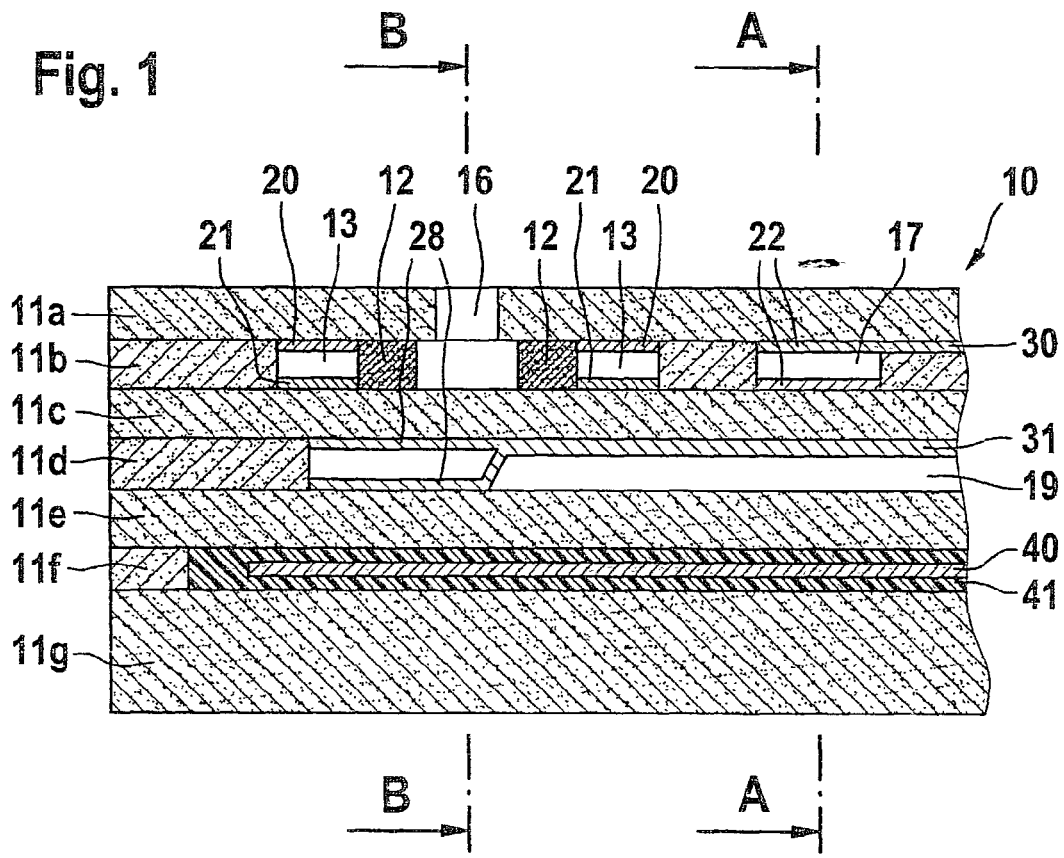
FIG. 1 shows a longitudinal section of a sensor element for determining the oxygen concentration of a gas mixture according to a first embodiment of the present invention. In this embodiment, the internal gas space in which the outer pumping electrode is located is incorporated into the same layer plane as another internal gas space that is in contact with the gas mixture under analysis.

FIG. 1 shows a basic structure of a first embodiment of the present invention. A planar sensor element of an electrochemical gas sensor is designated as 10, the element having a plurality of oxygen ion-conducting solid electrolyte layers 11$a$, 11$b$, 11$c$, 11$d$, 11$e$, 11$f$ and 11$g$, for example. In this case, solid electrolyte layers 11$a$ to 11$g$ are designed as ceramic sheets and form a planar ceramic body. They are composed of an oxygen-ion-conducting solid electrolyte material such as $ZrO_2$ that has been stabilized or partially stabilized with $Y_2O_3$.

The integrated form of the planar ceramic body of sensor element 10 is manufactured by laminating together ceramic sheets imprinted with functional layers and then sintering the laminated structure by a method that is known per se.

Sensor element 10 includes two gas spaces, an internal gas space 13 and a reference gas duct 19. Reference gas duct 19 is open at one end and is in contact with a reference gas atmosphere. Internal gas space 13 is annular in design, for example, and is connected to the gas mixture atmosphere via an opening 16. Opening 16 is placed in solid electrolyte layer 11$a$ preferably at a right angle to the surface of sensor element 10.

In internal gas space 13, there is an inner pumping electrode 20, which, being adapted to the annular geometry of internal gas space 13, is also annular in design. Opposite inner pumping electrode 20 in internal gas space 13 there is a measuring electrode 21 which may be short-circuited with inner pumping electrode 20. The latter is also annular in design, for example. Associated reference electrode 28 is located in reference gas duct 19. Alternatively, reference electrode 28 may also be designed as two electrodes and contacted via a printed conductor 31. Measuring and reference electrodes 21, 28 together form a Nernst cell or concentration cell.

Within measuring gas space 13, a porous diffusion barrier 12 is located upstream from inner pumping electrode 20 and measuring electrode 21 in the diffusion direction of the test gas. Porous diffusion barrier 12 creates diffusion resistance with respect to the gas diffusing towards electrodes 20, 21.

In addition, a resistance heater 40 is integrated into solid electrolyte layer 11f, for example, and embedded in electric insulation 41 made of $Al_2O_3$, for example. Sensor element 10 is heated by resistance heater 40 to the appropriate operating temperature of 750° C., for example.

Inner pumping electrode 20 forms a pumping cell together with an outer pumping electrode 22, which is contacted by a printed track 30. Outer pumping electrode 22 is located in a second internal gas space 17. A pumping voltage is applied to pumping electrodes 20, 22 so that oxygen transfer takes place between inner and outer pumping electrodes 20, 22. A constant oxygen partial pressure is established in internal gas space 13 by the oxygen transfer, the second internal gas space 17 serving as an oxygen reservoir. The pumping voltage applied to pumping cell 20, 22 is varied so that a largely constant potential difference of 450 mV, for example, is applied to the concentration cell formed by measuring electrode 21 and reference electrode 28. The pumping current flowing between electrodes 20, 22 of the pumping cell is used as a measuring signal that is proportional to the oxygen concentration in the exhaust gas.

Figure 2:
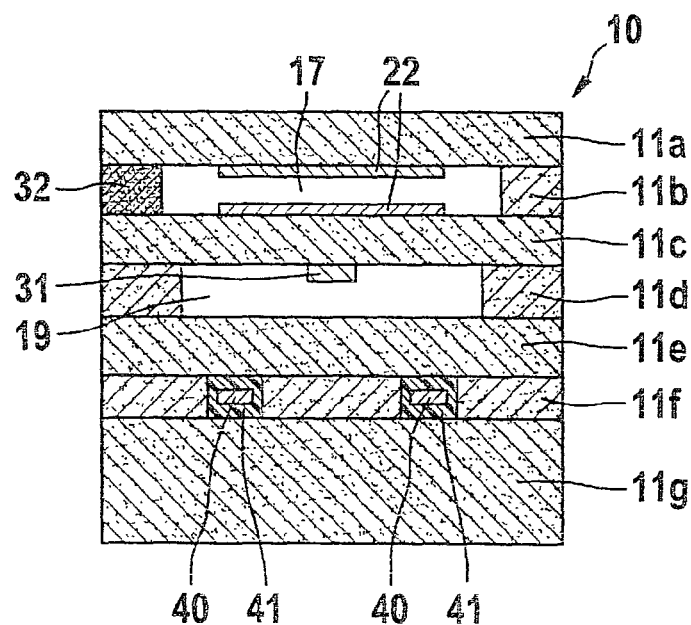
FIG. 2 illustrates a cross section through the sensor element shown in FIG. 1 along line A—A.

Outer pumping electrode 22 is located in the second internal gas space 17, which is located preferably in the same layer plane 11b as internal gas space 13, and, alternatively, may also be provided as two electrodes. In order to prevent a potential overpressure in the second internal gas space 17, the latter, as shown in FIG. 2, may be in contact with the gas mixture surrounding the sensor element via a diffusion resistor in the form of another diffusion barrier 32. The porosity of diffusion barrier 32 is designed so that the penetration of the gas mixture is made much more difficult and outer pumping electrode 22 is effectively protected against damage by aggressive gas constituents of the gas mixture. This effect may be reinforced by filling, at least partially, the second internal gas space 17 with porous ceramic material.

Another alternative for preventing a potential overpressure in the second internal gas space 17, is to design lead 30 of outer pumping electrode 22 to be porous so that in this way a portion of the gas mixture present in the second internal gas space 17 is able to escape.

In order to guarantee that thermodynamic equilibrium of the gas mixture components is established on the electrodes, all the electrodes that are used are made of a catalytically active material such as platinum. The electrode material for all electrodes is inserted in the form of a cermet by a method that is known per se, in order to be sintered together with the ceramic sheets.

Figure 3:
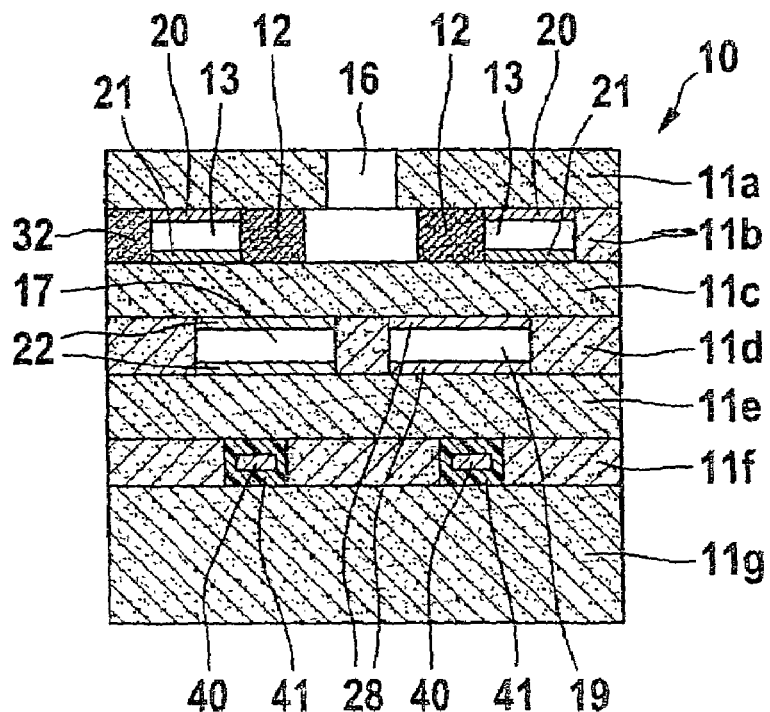
FIG. 3 illustrates a cross section through the sensor element shown in FIG. 1 along line B—B.

FIG. 3 illustrates a cross section through a sensor element shown in FIG. 1 along section plane B—B according to a second embodiment of the present invention. In this embodiment, the second internal gas space 17 is incorporated into layer plane 11d, in which reference gas duct 19 is also located. Second internal gas space 17 is aligned parallel to reference gas duct 19, and like the latter it is in contact with a reference gas atmosphere. This design corresponds to a double reference gas duct that is divided in its longitudinal direction.

Figure 4:
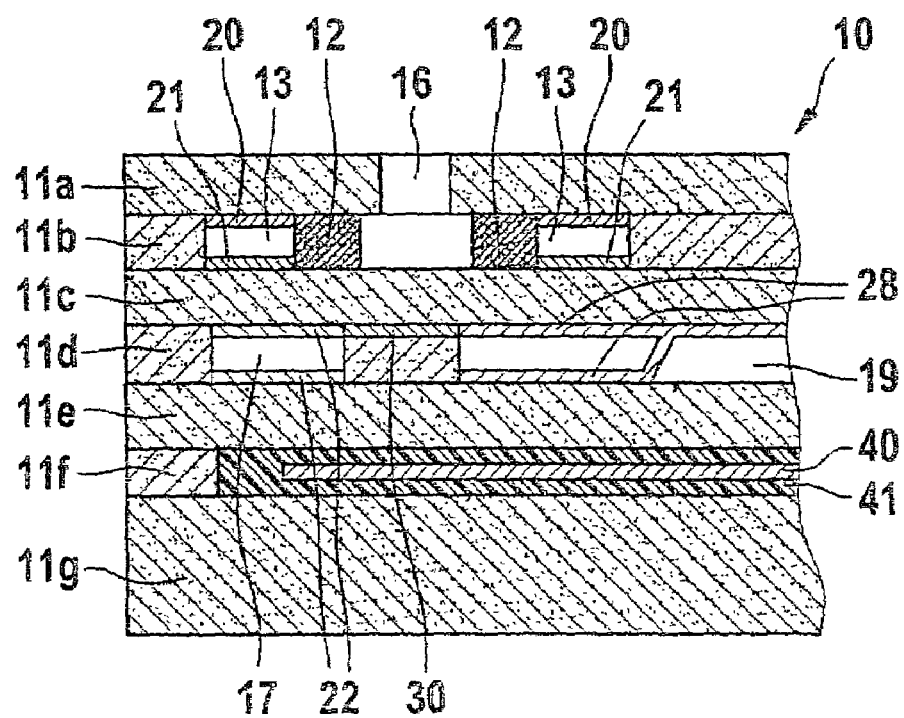
FIG. 4 shows a longitudinal section according to another embodiment, in which the internal gas space in which the outer pumping electrode is located is incorporated into the same layer plane of the sensor element as a separate reference gas duct.

FIG. 4 shows a sensor element according to a third embodiment of the present invention as a variant of the sensor element illustrated in FIG. 3.

Second internal gas space 17, which includes outer pumping electrode 22, is located in layer plane 11d, in which reference gas duct 19 is located. In this embodiment, second internal gas space 17 is not designed in the form of a separate reference gas duct but as a gas space having no direct contact with a reference gas atmosphere. In order to prevent potential overpressure during operation of the sensor element, second internal gas space 17, as already described in the case of the sensor element shown in FIG. 2, may be vented via another diffusion barrier or a porous lead of electrode 22.

Figure 5:
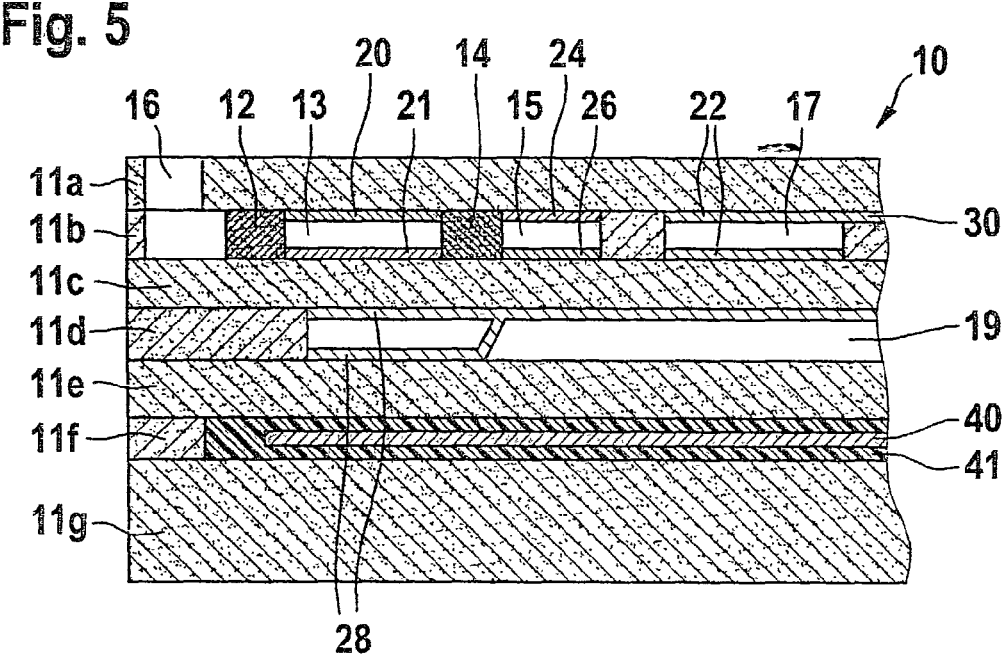
FIG. 5 is a first illustration of longitudinal sections through sensor elements for determining the nitrogen oxide concentration, for example, of a gas mixture under analysis.
Figure 6:
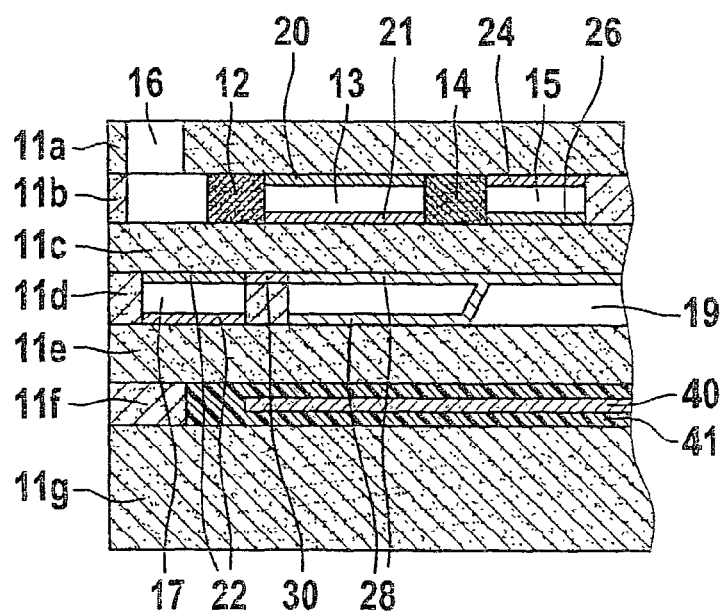
FIG. 6 is a second illustration of longitudinal sections through sensor elements for determining the nitrogen oxide concentration, for example, of a gas mixture under analysis. The internal gas space in which the outer pumping electrode is located is incorporated in one case in the same layer plane as another internal gas space in contact with the gas mixture under analysis and in another case in the layer plane of a reference gas duct.

Whereas FIGS. 1 through 4 describe and show examples of sensor elements for determining the oxygen concentration of a gas mixture, FIGS. 5 and 6 illustrate sensor elements that are used for the determination of nitrogen oxides, for example.

The sensor element illustrated in FIG. 5 according to a fourth embodiment has another internal gas space 15 that is in contact, by way of a second diffusion barrier 14, with internal gas space 13, which in this case is not annular in design.

In the other internal gas space 15, there is another inner electrode 24, which together with outer electrode 22 or reference electrode 28 forms a second pumping cell. This pumping cell is used to further reduce the oxygen concentration of the gas mixture diffusing in from the first internal gas space 13. In the other internal gas space 15, moreover, a third inner pumping electrode 26 is provided, which, together with reference electrode 28, forms a third electrochemical pumping cell. Third pumping cell 26, 28 is used to detect the gas that is to be determined, in which case the gas that is to be determined decomposes on the surface of inner pumping electrode 26, and the oxygen that is released or remains after the reaction is pumped off. The pumping current flowing between electrodes 26, 28 is used as the measure for the concentration of the gas that is to be determined.

In order to guarantee that no decomposition of the gas that is to be determined occurs on electrodes 20, 21, 24, electrodes 20, 21, 24 of the sensor element illustrated in FIG. 5 are fabricated from a catalytically inactive material. This may be gold or a gold-platinum alloy, for example. In contrast, electrode 26 is designed to be catalytically active and is made of rhodium or a platinum-rhodium alloy, for example.

Second internal gas space 17 is located, as in the sensor element shown in FIG. 5, in layer plane 11b, which also includes internal gas spaces 13, 15. Outer pumping electrode 22 is located in internal gas space 17 and may be in contact with the gas mixture via another porous diffusion barrier by analogy with the sensor element shown in FIG. 1. In this case as well, an alternative venting of the second internal gas space 17 is possible via a porously designed lead 30 of electrode 22.

FIG. 6 illustrates a variant of the sensor element shown in FIG. 5, in which variant second internal gas space 17 is integrated into layer 11d instead of being in the solid electrolyte layer 11b. Venting of the second internal gas space 17 may also be effected in this case by way of another diffusion barrier or by way of a porous lead of electrode 22. Another possibility is to design the second internal gas space 17 as part of a reference gas duct that is divided lengthwise, similarly to with the embodiment shown in FIG. 3.

The present invention is not limited to the embodiments shown in the figures. Instead, a plurality of additional applications is conceivable. This applies, for example, to electrochemical gas sensors for determining hydrocarbons, hydrogen, methane, ammonia, etc., as long as they have an electrochemical pumping cell.

What is claimed is:

1. A solid electrolyte-based sensor element of a gas sensor for determining a gas component in a gas mixture, comprising:
   an electrochemical pumping cell configured to establish a constant oxygen partial pressure, the electrochemical pumping cell including a first electrode arrangement and a second electrode arrangement, the first electrode arrangement and the second electrode arrangement being located in internal gas spaces of the sensor element, wherein:
      the internal gas space in which the first electrode arrangement is located is designed as a reference gas duct that is divided in a longitudinal direction, the first electrode arrangement being located in one section of the reference gas duct and a reference electrode arrangement being located in another section of the reference gas duct; and
      both sections of the reference gas duct are located largely in the same layer plane of the sensor element.

2. The sensor element as recited in claim 1, wherein the sensor element is for determining a concentration of at least one of oxygen and a nitrogen oxide in an exhaust gas of an internal combustion engine.

3. The sensor element as recited in claim 2, wherein the gas component is determined on the basis of a pumping current configured to flow between a third electrode arrangement and the reference electrode arrangement.

4. The sensor element as recited in claim 3, wherein the second electrode arrangement includes a catalytically inactive electrode.

5. The sensor element as recited in claim 1, wherein the electrochemical pumping cell is configured to adjust an oxygen partial pressure on the second electrode arrangement through an oxygen transfer between the first electrode arrangement and the second electrode arrangement.

6. The sensor element as recited in claim 5, wherein an applied varying voltage is configured to control the oxygen transfer.

7. The sensor element as recited in claim 1, further comprising:
   a diffusion resistor, wherein the internal gas space in which the first electrode arrangement is located is connected to the gas mixture via the diffusion resistor.

8. The sensor element as recited in claim 7, wherein the internal gas space in which the first electrode arrangement is located is filled predominantly with a porous material.

9. The sensor element as recited in claim 1, wherein the internal gas space in which the first electrode arrangement is located is in contact with a reference gas atmosphere.

10. The sensor element as recited in claim 9, wherein the internal space in which the first electrode arrangement is located does not contact the gas mixture.

11. The sensor element as recited in claim 1, further comprising:
    a lead for achieving an electrical contacting of the first electrode arrangement and including a porous material.

12. The sensor element as recited in claim 1, wherein at least one of the internal gas spaces is annularly shaped.

13. The sensor element as recited in claim 1, further comprising:
    a measuring electrode arrangement, the combination of the measuring and reference electrode arrangements configured to form a Nernst cell.

14. The sensor element as recited in claim 1, wherein the first electrode arrangement includes one of one and two pumping electrodes.

15. The sensor element as recited in claim 1, wherein the reference electrode arrangement includes one of one and two reference electrodes.

* * * * *